United States Patent [19]

Drucker

[11] Patent Number: 5,952,301
[45] Date of Patent: Sep. 14, 1999

[54] COMPOSITIONS AND METHODS FOR ENHANCING INTESTINAL FUNCTION

[75] Inventor: Daniel J. Drucker, Toronto, Canada

[73] Assignee: 1149336 Ontario Inc., Toronto, Canada

[21] Appl. No.: 08/763,177

[22] Filed: Dec. 10, 1996

[51] Int. Cl.[6] .................................................. A61K 38/00
[52] U.S. Cl. .............................. 514/12; 435/4; 435/240.1; 435/287; 530/399; 530/308
[58] Field of Search .................................. 514/12; 435/4, 435/240.1, 287; 530/399, 308

[56] References Cited

U.S. PATENT DOCUMENTS 5,288,703  2/1994  Wilmore ....................................... 514/2
5,482,926  1/1996  Gluckman et al. ......................... 514/12

OTHER PUBLICATIONS

Drucker et al., *Proc. Natl. Acad. Sci.* USA, 93(15), pp. 7911–7916, 1996.
Zhang et al., *J. Surg. Res.*, 59(1), pp. 6–12, 1995.
Read et al., *Int. Congr. Ser.—Excerpta Med.*, 1056, 409–16, 1994

*Primary Examiner*—Cecilia J. Tsang
*Assistant Examiner*—C. Delacroix-Muirheid
*Attorney, Agent, or Firm*—Pennie & Edmonds LLP

[57] ABSTRACT

GLP-2 stimulates the growth of both small intestine and large intestine tissue when administered in conjunction with other peptide hormones. The invention provides pharmaceutical compositions of GLP-2 with at least one other peptide hormone, methods of enhancing the growth of both small and large intestine tissue and of ameliorating nutritional or gastrointestinal disorders by increasing serum levels of GLP-2 and at least one other peptide hormone, and kits for performing the methods of the invention.

7 Claims, 1 Drawing Sheet

COMPOSITIONS AND METHODS FOR ENHANCING INTESTINAL FUNCTION

This invention relates to glucagon-related peptides and their use in combination with other peptide hormones, for the prevention or treatment of nutritional or gastrointestinal disorders.

BACKGROUND TO THE INVENTION

Glucagon-like peptide-2 (GLP-2) is a 33 amino acid peptide expressed in a tissue-specific manner from the pleiotropic glucagon gene. GLP-2 shows remarkable homology in terms of amino acid sequence to glucagon and Glucagon-like peptide-1 (GLP-1). Further, different mammalian forms of GLP-2 are highly conserved. For example the human GLP-2 and degu (a south American rodent) GLP-2 differ from rat GLP-2 by one and three amino acids respectively. Recently it was demonstrated that GLP-2 is an intestinotrophic peptide hormone (Drucker et al., (1996) PNAS, 93:7911–7916). When given exogenously, GLP-2 can produce a marked increase in the proliferation of small intestinal epithelium of the test mice, apparently with no undesirable side effects. Subsequently it was shown that peptide analogs of native GLP-2 with certain modifications to the peptide sequence possess enhanced intestinotrophic activity (see co-pending application U.S. Ser. No. 08/669,791, incorporated herein by reference). Moreover, GLP-2 has also been shown to increase D-Glucose maximal transport rate across the intestinal basolateral membrane (Cheeseman and Tseng (1996) American Journal of Physiology 271:G477–G482).

A number of peptide hormones, structurally unrelated to GLP-2, have been demonstrated to have varying degrees of intestinotrophic activity. For example, Insulin-Like Growth Factor-2 (IGF-2) has been shown to promote mitosis of the crypt cells of the small intestine in vivo (U.S. Pat. No. 5,482,926). Insulin-Like Growth Factor-1 (IGF-1), which shares 64% sequence identity with IGF-2, and peptide analogs thereof have also been shown to increase the growth of gut tissue in vivo (WO 91/12018). Growth Hormone (GH) has been shown to have a number of physiological effects, including increasing proliferation of the intestinal mucosa (see, for example, Willmore, U.S. Pat. No. 5,288,703) thereby enhancing the absorptive capacity of the gut. However, none of the above peptide hormones possess the efficacy or specificity of GLP-2 in promoting proliferation of the intestine epithelium.

SUMMARY OF THE INVENTION

The invention is based, in part, on the discovery that GLP-2 acts synergistically with the peptide hormones IGF-1 and/or GH to promote the proliferation of cells in the large intestine. Furthermore, coadministration of GLP-2 with either IGF-1 or GH results in a proliferation of the cells of the small intestinal epithelium and consequent increased small intestine mass. The intestinotrophic effects on the small and large intestines of this combination therapy are greater than that seen with any one of GLP-2, IGF-1 or GH alone. An additional aspect of the invention is the coadministration of GLP-2 with IGF-2 to promote growth of small and/or large intestine tissue.

Therefore, one aspect of the invention is a composition for promoting the growth of small and/or large intestine tissue in a mammal which comprises GLP-2, or an intestinotrophic analog of GLP-2, in admixture with at least one other peptide hormone selected from the group consisting of IGF-1, IGF-2, and GH, and a pharmaceutically acceptable carrier. These compositions of the invention may alternatively include analogs of GLP-2, IGF-1, IGF-2 and/or GH which exhibit intestinotrophic activities.

In another aspect, the invention provides a method of promoting the growth of small and/or large intestine tissue in a mammal, comprising treating the mammal to elevate serum levels of GLP-2, or an intestinotrophic analog of GLP-2, and at least one other peptide hormone selected from the group consisting of IGF-1, analogs of IGF-1, IGF-2, analogs of IGF-2, GH, and analogs of GH. Such methods of the invention include co-administering to a mammal an effective amount of GLP-2 and an effective amount of at least one other peptide hormone selected from the group consisting of IGF-1, analogs of IGF-1, IGF-2, analogs of IGF-2, GH, and analogs of GH, treating the mammal with hormones or small organic molecules which act to elevate serum levels of GLP-2, IGF-1, IGF-2, and/or GH, and performing gene therapy to induce cells in the mammal to endogenously produce GLP-2, IGF-1, IGF-2, and/or GH or to engineer cells to produce GLP-2, IGF-1, IGF-2, or GH, alone or in combination, that may then be implanted in a mammal to produce the desired biological effect.

Also provided by the invention is a method of ameliorating a nutritional or gastrointestinal disorder, comprising treating the mammal to elevate serum levels of GLP-2, or an intestinotrophic analog of GLP-2, and at least one other peptide hormone selected from the group consisting of IGF-1, analogs of IGF-l, IGF-2, analogs of IGF-2, GH, and analogs of GH.

The compositions and methods of the invention are useful for restoring or maintaining gastrointestinal function, for promoting the healing and regrowth of injured or ulcerated/inflamed intestinal mucosa, for reducing the risk of enteric disease, for enhancing the nutritional status of a mammal, and for the treatment or prevention of nutritional or gastrointestinal disorders in a mammal, particularly a human.

Further, the methods and compositions of the invention are useful for promoting villous growth in patients suffering from a disease such as celiac disease, post-infectious villous atrophy and short gut syndromes.

Alternatively, the compositions and methods of the invention can be used to promote proliferation of the small and large intestine in a healthy mammal, e.g., to enable increased absorption of nutrients in cattle allowing earlier weaning or increased milk and meat production.

In yet another aspect of the invention, there is provided a use of GLP-2, or intestinotrophic analogs of GLP-2, for the manufacture of a pharmaceutical or veterinary preparation for the enhancement of large intestine tissue growth. In a particularly preferred aspect of the invention, such preparations also include another peptide hormone selected from the group consisting of IGF-1, analogs of IGF-1, IGF-2, analogs of IGF-2, GH, and analogs of GH.

Still further, the invention provides kits comprising GLP-2, or intestinotrophic analogs of GLP-2, and at least one other peptide hormone selected from the group consisting of IGF-1, analogs of IGF-1, IGF-2, analogs of IGF-2, GH, and analogs of GH. Such compositions are provided in a therapeutically effective unit dose or multi-dose amount.

Also provided by the instant invention is a method for promoting the growth of gastrointestinal tissue or cells which comprises the step of culturing said tissue or cells in a culturing medium containing a growth promoting combination of both GLP-2, or an intestinotrophic GLP-2 analog, and at least one other peptide hormone selected from the group consisting of IGF-1, analogs of IGF-1, IGF-2, analogs of IGF-2, GH, and analogs of GH. These methods may be performed on cells in culture and in vivo.

In yet another aspect of the invention, there is provided a method in which treatment of a patient to restore gastrointestinal tissue is performed by the steps of (1) culturing tissue or cells derived from the patient with a tissue growth promoting amount of a combination of GLP-2 or an intestinotrophic GLP-2 analog, and at least one other peptide hormone selected from the group consisting of IGF-1, analogs of IGF-1, IGF-2, analogs of IGF-2, GH, and analogs of GH and then (2) implanting said tissue or cells in the patient to be treated.

Finally, the invention also provides a method for determining the intestinotrophic activity of a hormone when used in combination with GLP-2 which comprises the steps of: (1) coadministering the hormone with an intestinotrophic amount of GLP-2, or a GLP-2 analog, to a test mammal; (2) assessing the subsequent growth of small and large intestine tissue in the test mammal; and (3) determining whether the growth of small and/or large intestine tissue in the test mammal is enhanced relative to control mammals treated with GLP-2 alone.

BRIEF REFERENCE TO THE DRAWINGS

FIG. 1 illustrates measurements of the proximal jejunum crypt plus villus height (in AM) (Y-axis) in animals injected twice daily with the indicated hormones (except that GH was only given once daily) for 10 days, as described in Example 3 infra. The treatment groups were: PBS; rat GLP-2; [Gly 2]hGLP-2; IGF-1; GH-(Protropin-Growth Hormone); Insulin-like growth factor-1 analogue (LRIGF-1); IGF-1+rGLP-2; GH+rGLP-2; LRIGF-1+rGLP-2; IGF-1+(Gly 2) hGLP-2; GH+[Gly 2) hGLP-2; and LRIGF-1+ [Gly2]hGLP-2.

DETAILED DESCRIPTION OF THE INVENTIONS

Figure 1:
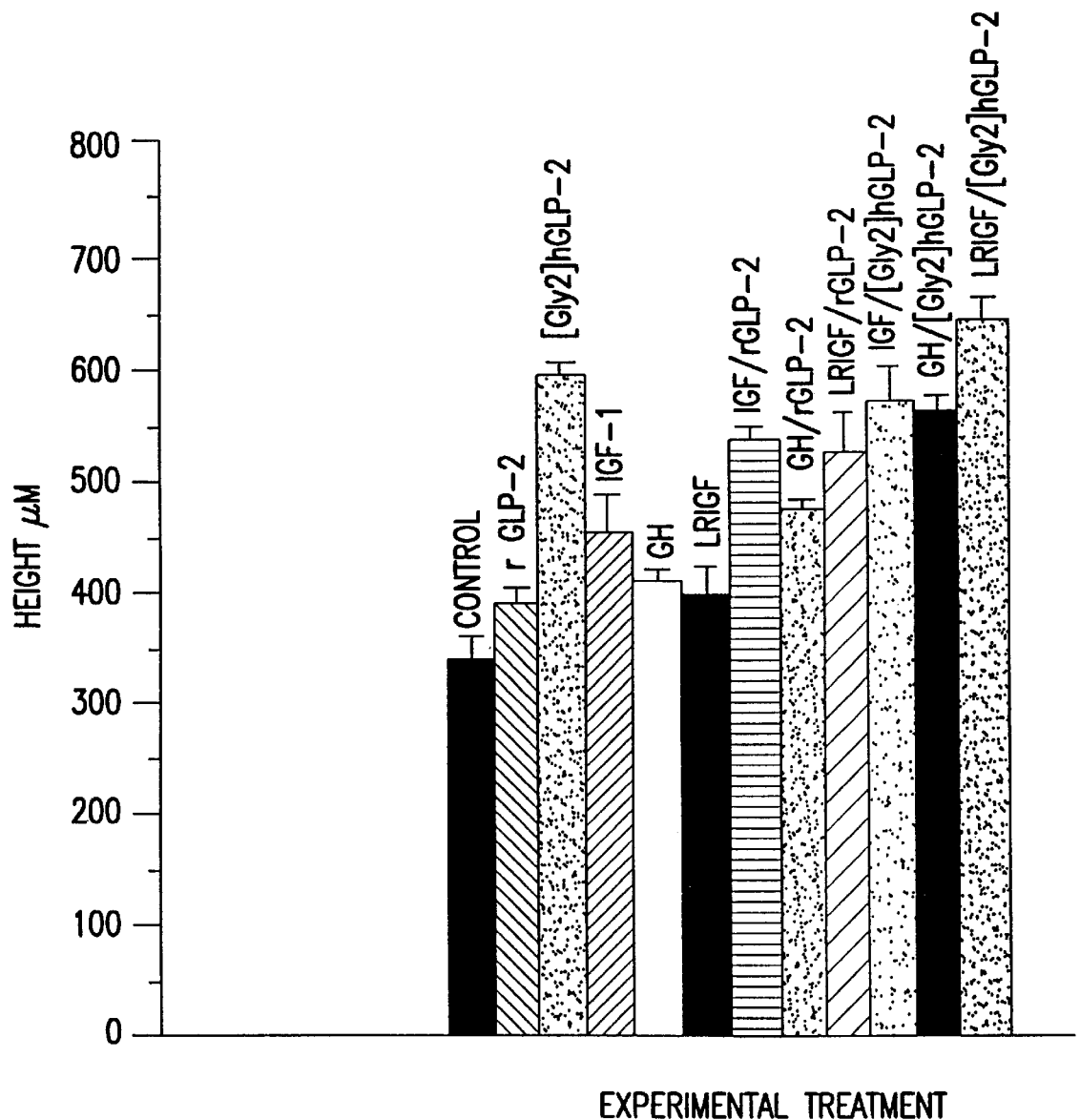

The invention relates to therapeutically useful combinations of GLP-2 and at least one other intestinotrophic peptide hormone selected from the group consisting of IGF-1, IGF-2, and GH. Surprisingly, it has been found that GLP-2 (and its analogs) administered alone to a mammal induces the growth of the small intestine. However, when GLP-2 is administered in combination with at least one other peptide hormone selected from the group IGF-1, IGF-2, and GH, clear effects on the growth of both small and large intestine tissue are observed.

More particularly, the invention relates to the therapeutic and related uses of GLP-2 when co-administered with at least one other peptide hormone selected from the group consisting of IGF-1 and GH. Even more particularly, the invention relates to the uses of the above-mentioned combinations to enhance intestinal functioning. Most particularly, the invention relates to the therapeutic and related uses of the above-mentioned combinations to promote the proliferation of the epithelial cells of the small and large intestine.

Unless otherwise specified, the term "GLP-2" refers collectively herein to the various naturally produced forms of GLP-2, particularly mammalian forms. The invention also encompasses those analogs of GLP-2 which exhibit intestinotrophic activity. Analogs of GLP-2 can be tested for intestinotrophic activity using the mouse model described herein and in co-pending application U.S. Ser. No. 08/631, 273. Briefly, this testing involves a 10 to 14 day regimen of twice a day (b.i.d) subcutaneous injection of 2.5 mg of the GLP-2 analog (in PBS) per kg body weight with control matched untreated animals receiving PBS alone. Alternatively, the analogs may be administered once a day, or every other day. Upon completion of the regimen the animals are sacrificed and their intestines removed and weighed. In this manner, the effect of analogs of GLP-2 on the intestine can be assessed.

Guidance on particular analogs and variants of GLP-2 that may be usefully employed in the present invention, and guidance on how to produce others, is provided in co-pending applications U.S. Ser. Nos. 08/632,533 and 08/631,273, the disclosures of which are incorporated herein by reference. Briefly, any substitution, addition or deletion of GLP-2 that does not destroy the intestinotrophic activity of GLP-2 may be usefully employed in this invention. In preferred embodiments the GLP-2 analogs are at least as intestinotrophic as native human GLP-2. In the most preferred embodiments, the GLP-2 analog has enhanced intestinotrophic activity compared with native human GLP-2. For example, such analogs may exhibit enhanced serum stability, enhanced receptor binding and enhanced signal transducing activity. Other modifications to GLP-2 and GLP-2 analogs that may usefully be employed in this invention are those which render the molecule resistant to oxidation.

The GLP-2 analogs are suitably analogs of either human GLP-2 (hGLP-2) or rat GLP-2 (rGLP-2). In a preferred embodiment of the invention, rat or human GLP-2 is altered at position 2 to confer DPP-IV resistance by substituting a Gly for an Ala. Human GLP-2 having Gly substituted for Ala at position 2 is referenced herein as (Gly 2] hGLP-2.

Similarly, the terms "IGF-1", "IGF-2" and "GH" as used herein encompass effective analogs and variants of the naturally produced peptides as well as the native peptides. Guidance on particular analogs and variants of IGF-1, IGF-2, and GH that may usefully be employed in the present invention is provided in the following publications which are incorporated herein by reference: Vanderhoof et al. (1992) Gastroenterology 102:1949–1956; Steeb et al. (1994) Am. J. Physiol. 266:G1090–G1098; and Jones et al. (1995) Endocrine Reviews 16:3–34; Conlon et al. (1995) Journal of Endocrinology 146:247–253; Francis et al. (1993) Biochemical Journal 293:713–719; Lewis et al. WO 93/20836; and Bozyczko-Coyne et al. WO 93/08826.

Secretagogues, factors capable of enhancing endogenous production, of the subject peptide hormones may also be included as part of a therapeutic regimen, either in lieu of or as a supplement to the subject peptide hormone the release of which it stimulates. Thus, the inclusion of such factors, which are well known to those of ordinary skill in the art, is within the scope of the invention. For example, production of endogenous GH is increased by growth hormone releasing factor (GHRF) and by arginine. Similarly, the skilled artisan will be aware that compounds such as small molecules, which act on the appropriate receptor to cause an increase in the serum levels of any of the subject peptide hormone, could be usefully employed in the present invention.

As used herein, a compound, such as a peptide, is said to be "co-administered" or in "combination" with another compound when either the physiological effects of both compounds, or the elevated serum concentration of both compounds can be measured simultaneously. With compounds that increase the level of endogenous production, the serum concentration of the endogenously produced hormone and the other administered agent can also be measured simultaneously when "co-administered" or in "combination". Thus, compounds may be administered either simultaneously, as separate or mixed compositions, or they may be administered sequentially provided that a constant elevation of their levels in serum results.

Unless otherwise stated the terms "combination therapy" and "combination treatments" are used herein to describe a therapeutic regimen involving co-administration of the subject peptide hormones which results in an enhancement of the nutritional status, or an increase in intestinal mass, of a patient.

As used herein, the terms "enhanced nutritional status" and "enhanced gut functioning" are defined as any increase in bodily uptake of nutrients over pretreatment levels. Such nutrients include, but are not limited to, carbohydrates, protein and amino acids, fat, cholesterol and fat-soluble vitamins, water soluble vitamins, and minerals. Minerals, the uptake of which can be increased by the methods of the present invention, include, but are not limited to, Na, Ca, Mg, K, Zn, and Fe. Vitamins, the absorption of which can be increased by the present invention include fat soluble vitamins such as vitamins A, D, E and K as well as water soluble vitamins such as $B^{12}$ and folic acid.

As used herein the term "patient" is intended to include, but is not limited to humans, livestock and pets.

A mammal is said to be suffering from disorders, diseases and medical conditions of the gut when the absorptive properties of the gut of the mammal are diminished, and/or when inflammation or injury to the gastrointestinal tract is present so as to cause discomfort and illness. A variety of tests can be employed to determine if a mammal is suffering from malabsorption syndrome. These include stool fat content, xylose absorption, gastrointestinal x-ray studies, small intestine biopsy test, the Schilling test for vitamin $B^{12}$ absorption and the secretin test.

In one aspect of the invention, GLP-2 is provided for administration to patients in admixture with at least one other peptide hormone selected from the group consisting of IGF-1, IGF-2, and GH in pharmaceutically acceptable form (for example, as a preparation that is sterile filtered through a 0.22 m filter and substantially pyrogen free). Desirably, the peptides to be admixed migrate as single peaks on HPLC.

The particular forms of GLP-2, IGF-1, IGF-2 and GH selected for the invention can be prepared by a variety of techniques well known for generating peptide products. Those forms of GLP-2, IGF-1, IGF-2 and GH that occur naturally can of course be obtained by extraction from the natural source, using an appropriate combination of protein isolation techniques. For example as described by Buhl et al., (1988) J. Bio. Chem., 263(18): 8621–8624, porcine GLP-2 isolation and purification is achieved from acid-ethanol extracts of ileal mucosa by a combination of size selection and HPLC-based fractionation, with the aid of antibody raised against synthetic proglucagon 126–159, to monitor work-up. Similarly, GH can be extracted from cadavers as described in U.S. Pat. No. 2,974,088.

As an alternative to extraction, those forms of GLP-2, IGF-1, IGF-2 and GH that incorporate only L-amino acids can be produced reproducibly and in commercial quantities by application of recombinant DNA technology. For this purpose, nucleic acids coding for the desired form of GLP-2, IGF-1 (see, for example, U.S. Pat. No. 5,288,931), IGF-2 and GH (see, for example, Goeddel et al. (1979) Nature 281:544–548) are incorporated expressibly in a cellular host, which is then cultured under conditions appropriate for expression of that particular peptide or protein. A variety of gene expression systems have been adapted for this purpose, and typically drive expression of the desired gene from expression controls used naturally by the chosen host. Because GLP-2, IGF-1, IGF-2 and GH do not require post translational modification for activity, their production may conveniently be achieved in bacterial hosts such as E. coli. For such production, DNA coding for the selected GLP-2, IGF-1, IGF-2 or GH may usefully be placed under expression controls of the lac, trp or PL genes of E. coli. As an alternative to expression of DNA coding for the GLP-2, IGF-1, IGF-2 or GH per se, the host can be adapted to express GLP-2, IGF-1, IGF-2 or GH as a fusion protein in which the GLP-2, IGF-1, IGF-2 or GH is linked releasably to a carrier protein that facilitates isolation and stability of the expression product.

For therapeutic use, the peptide hormones chosen for use in combination therapy are formulated with at least one carrier that is pharmaceutically acceptable and is appropriate for delivering the peptides by the chosen route of administration. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Penn., 1985, for guidance on drug formulations generally. In one embodiment of the invention, the compounds are formulated for administration by infusion or by injection, either subcutaneously or intravenously, and are accordingly utilized as aqueous solutions in sterile and pyrogen-free form and optionally buffered to a slightly acidic or physiological pH. Thus, the compounds may be administered in distilled water or, more desirably, in saline, buffered saline or 5% dextrose solution. Water solubility of these compounds may be enhanced, if desired, by incorporating a solubility enhancer, such as the inclusion of acetic acid for GLP-2 formulations.

The subject invention also provides for various peptide hormone conjugates. The peptide hormone compositions of the invention comprise peptide hormone covalently linked to one or more water soluble polymers. Water soluble polymers, especially polyethylene glycol, have been conjugated to proteins so as to provide additional desirable properties while retaining, at least in part, the growth inducing properties of the peptide hormone. These desirable properties include increased solubility in aqueous solutions, increased stability in storage, reduced immunogenicity, increased resistance to proteolytic degradation, and increased in vivo half-life. Water soluble polymers suitable for use in the subject compositions include polyethylene glycol homopolymers, polypropylene glycol homopolymers, copolymers of ethylene glycol with propylene glycol, wherein said homopolymers and copolymers are unsubstituted or substituted at one end with an alkyl group, polyoxethylated polyols, polyvinyl alcohol, polysaccharides, polyvinyl ethyl ethers, and α,β-poly[(2-hydroxyethyl)-DL-aspartamide]. Polyethylene glycol is particularly preferred. Methods of making water-soluble polymer conjugates of proteins are described in, among other places, U.S. Pat. No. 4,179,337; U.S. Pat. No. 4,609,546; U.S. Pat. No. 4,261,973; U.S. Pat. No. 4,055,635; U.S. Pat. No. 3,960,830; U.S. Pat. No. 4,415,665; U.S. Pat. No. 4,412,989; U.S. Pat. No. 4,002,531; U.S. Pat. No. 4,414,147; U.S. Pat. No. 3,788,948; U.S. Pat. No. 4,732,863; U.S. Pat. No. 4,745,180; EP No. 152,847; EP No. 98,110 (published Jan. 11, 1984); JP No. 5,792,435.

Another aspect of the invention is formulations that provide for the sustained release of peptide hormones.

Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al. (1992), Polymers for Advanced Technologies 3:279–292. Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of peptide hormones. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of the compositions of the invention, e.g., near or in the small or large bowel, etc.

For use in stimulating intestine growth in a mammal including a human, the present invention provides in one of its aspects a package, in the form of a sterile-filled vial or ampoule, that contains a tissue growth promoting amount of GLP-2 in admixture with at least one other peptide hormone selected from the group consisting of IGF-1, IGF-2 and GH in either unit dose or multi-dose amounts, wherein the package incorporates a label instructing use of its contents for the promotion of gastrointestinal functioning, e.g. for promotion of growth of the small intestine or large intestine or both. In one embodiment of the invention, the package contains GLP-2 and at least one other peptide hormone selected from the group consisting of IGF-1, IGF-2 and GH, and the desired carrier, as an administration-ready formulation. Alternatively, and according to another embodiment of the invention, the package provides the GLP-2 and at least one other peptide hormone selected from the group consisting of IGF-1, IGF-2 and GH in a form, such as a lyophilized form, suitable for reconstitution in a suitable carrier, such as buffered saline. In yet another embodiment, the package is a sterile-filled vial or ampoule containing an injectable solution which comprises an effective amount of GLP-2 and at least one other peptide hormone selected from the group consisting of IGF-1, IGF-2 and GH dissolved in an aqueous vehicle.

According to the present invention, the GLP-2 in combination with at least one other peptide hormone selected from the group consisting of IGF-1, IGF-2 and GH is administered to treat patients that would benefit from enhanced gastrointestinal functioning. In one aspect, patient candidates are those who would benefit from proliferation of the epithelium of the small intestine tissue or large intestine or both. The effects of combination therapy on these tissues, as evidenced by the results presented herein, is dramatic and would clearly benefit those patients suffering from diseases or conditions marked by abnormalities in the small or large intestinal tract mucosa, which include ulcers and inflammatory disorders; congenital or acquired digestion and absorption disorders including malabsorption syndromes; and diseases and conditions caused by loss of small or large intestine mucosal function. In general, patients who would benefit from either increased intestinal mass or regeneration and healing of preexistent normal mucosal epithelium, and consequent increased intestine mucosal function, are candidates for treatment with the invention. For example, patients may be treated after a regimen of chemotherapy or radiotherapy, after a period of parenteral nutrition, after or during active gastrointestinal disease, or if the patient is a premature infant with insufficient maturation of the gastrointestinal tract, and/or inflammation of the GI tract as exemplified by the condition necrotizing enterocolitis.

For convenience a non-exhaustive list of conditions of the small and large intestine that may usefully be treated by the subject combinations, is provided in the following table:

TABLE I

Disorders Of The Small And Large Intestine

I. Inadequate absorptive surface
   A. Intestinal resection or bypass
      1. Mesenteric vascular disease with massive intestinal resection
      2. Regional enteritis with multiple intestine resections
      3. Jejunoileal bypass
      4. Intestine infarction from trauma, congenital abnormalities, volvulus, ischemia, etc.
      5. Necrotizing enterocolitis in the neonate
      6. short-gut syndrome
      7. cul-de-sac syndrome
   B. Gastroileostomy (inadvertent)
II. Lymphatic obstruction
   A. Intestinal lymphangiectasia
   B. Whipple's disease
   C. Lymphoma
III. Cardiovascular disorders
   A. Constrictive pericarditis
   B. Congestive heart failure
   C. Mesenteric vascular insufficiency
   D. Vasculitis
IV. Primary mucosal absorptive defects
   A. Inflaminatory or infiltrative disorders
      1. Regional enteritis
      2. Amyloidosis
      3. Scleroderma
      4. Lymphoma
      5. Radiation enteritis
      6. Eosinophilic enteritis
      7. Tropical or non-tropical sprue
      8. Infectious enteritis (bacterial, viral, or fungal, for example, cryptosporidium or isospora belli infection in HIV patients)
      9. HIV associated non-infectious idiopathic enteritis
      10. Post-infectious enteritis
      11. Collagenous sprue
      12. Nonspecific ulcerative jejunitis
      13. Mastocytosis
      14. Dermatologic disorders (e.g. dermatitis herpetiformis)
      15. Crohn's disease
      16. inflaminatory bowel disease
      17. Colitis
   B. Biochemical or genetic abnormalities
      1. Nontropical sprue (gluten-induced enteropathy) celiac sprue
      2. Disaccharide deficiency
      3. Hypogammaglobulinemia
      4. Abetalipoproteinemia
      5. Hartnup disease
      6. Cystinuria
      7. Monosaccharide malabsorption
V. Endocrine and metabolic disorders
   A. Diabetes mellitus
   B. Hypoparathyroidism
   C. Adrenal insufficiency
   D. Hyperthyroidism

TABLE I-continued

Disorders Of The Small And Large Intestine

E. Ulcerogenic tumor of the pancreas (Zollinger-Ellison syndrome, gastrinoma)
F. Carcinoid syndrome Numerous factors may be taken into consideration by a clinician when determining an optimal dosage for a given subject. Primary among these is the amount of peptide hormone normally produced by the body. Additional factors include the size of the patient, the age of the patient, the general condition of the patient, the particular disease being treated, the severity of the disease, the presence of other drugs in the patient, the in vivo activity of the peptide or peptide analog and the like. The trial dosages would be chosen after consideration of the results of animal studies and the clinical literature with respect to administration of peptide hormones and peptide hormone secretagogues. It will be appreciated by the person of ordinary skill in the art that information such as binding constants and Ki derived from in vitro binding competition assays may also be used in calculating dosages. The results presented herein below demonstrate that doses of the combination equivalent to about 0.1 mg/kg of GLP-2 and GLP-2 analogs twice daily, with approximately 2 mg/kg of IGF-1 twice daily and/or 1 mg/kg of GH once a day, co-administered over 10 days can generate very significant increases in both small intestine mass and large intestine mass. It is expected that much smaller doses, in the μg/kg range and perhaps into the ng/kg range, and perhaps shorter or longer duration or frequency of treatment, will also produce therapeutically useful results, e.g. a statistically significant increase, particularly in small intestine mass.

A typical human dose of a GLP-2 peptide would be from about 10 μg/kg body weight/day to about 10 mg/kg/day, preferably from about 50 Ag/kg/day to about 5 mg/kg/day, and most preferably about 100 μg/kg/day to 1 mg/kg/day. As the GLP-2 analogs of the invention can be up to 10 to even 100 times more potent than GLP-2, a typical dose of such a GLP-2 analog may be lower, for example, from about 100 ng/kg body weight/day to 1 mg/kg/day, preferably 1 μg/kg/day to 500μg/kg/day, and even more preferably 1 μg/kg/day to 100 μg/kg/day.

For administration of GH to a mammal, particularly humans, a dose range of 0.02–2.5 mg/kg/day may be used; preferably, GH doses may range from about 0.1–2 mg/kg/day. For administration of IGF's, dosages may be in the range of 1 μg to 1 g/kg/day. IGF-1 is preferably administered to humans in the range of about 0.03–10 mg/kg/day, more preferably from about 0.1–4 mg/kg/day, and most preferrably from around 0.5–1 mg/kg/day. Typical doses for IGF-2 are about 0.5–5 mg/kg/day. The dose required for analogues of IGF may be 20–50% less than naturally occurring IGF-1. Further, the dosage sizes and dosing regimen most appropriate for human use can be determined in properly designed clinical trials.

In another of its aspects, the invention provides for the treatment of patients as just identified using implanted intestinal cells that have been regenerated or stimulated to proliferate in vitro or in vivo prior to reimplantation or transplantation into a recipient. Conditioning of the cells ex vivo can be achieved simply by growing the cells or tissue to be transplanted in a medium that has been supplemented with a growth-promoting amount of the combinations and is otherwise appropriate for culturing of those cells. The cells can, after an appropriate conditioning period, then be implanted either directly into the patient or can be encapsulated using established cell encapsulation technology, and then implanted. Analogous procedures with other organs, such as the skin, are already fairly advanced clinically in human trials. For example, skin may be regenerated in vitro by taking skin cells from a donor, growing them up in tissue culture, and then transplanting back the expanded mass of skin back into a patient for therapeutic use (e.g. treatment of burns, ulcers, etc).

Further, the methods of the invention may be practiced using gene therapy. The recipient mammal's or patient's cells (which may be any type of cells but which are preferably fibroblasts or keratinocytes) can be engineered to express one or more of the subject growth factors, or combinations of GLP-2 with IGF-1 and/or IGF-2 and/or GH in vitro, followed by reimpantation, preferably in a capsule, in vivo for delivery of therapeutic amounts of these peptides. A variety of transfection techniques are currently available and used to transfer DNA in vitro into cells; including calcium phosphate-DNA precipitation, DEAE-Dextran transfection, electroporation, liposome-mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., 1987, Science 237:1476–1479; Morgan and Mulligan, U.S. Pat. No. 4,980,286); endothelial cells (WO89/05345); hepatocytes (WO89/07136; Wolff et al., 1987, Proc. Natl. Acad. Sci. USA 84:3344–3348; Ledley et al., 1987 Proc. Natl. Acad. Sci. 84:5335–5339; Wilson and Mulligan, WO89/07136; Wilson et al., 1990, Proc. Natl. Acad. Sci. 87:8437–8441); fibroblasts (Palmer et al., 1987, Proc. Natl. Acad. Sci. USA 84:1055–1059; Anson et al., 1987, Mol. Biol. Med. 4:11–20; Rosenberg et al., 1988, Science 242:1575–1578; Naughton & Naughton, U.S. Pat. No. 4,963,489); lymphocytes (Anderson et al., U.S. Pat. No. 5,399,346; Blaese, R. M. et al., 1995, Science 270:475–480); and hematopoietic stem cells (Lim, B. et al. 1989, Proc. Natl. Acad. Sci. USA 86:8892–8896; Anderson et al., U.S. Pat. No. 5,399,346).

As indicated by the working example below, gene therapy is a viable method of providing growth hormones for the practice of the invention. Specifically, described below is an experiment in which cells from a cell line which secretes all the glucagon peptides are implanted into a mouse. The implanted cells grow as a tumor which secretes GLP-2 and induces growth of the small intestine. Since GLP-2 is the only glucagon derived peptide known to markedly stimulate small intestine growth, the effect on small intestine growth observed in this experiment was most likely due to the secretion of GLP-2. Similarly, cells may be engineered to produce GLP-2 alone, and/or at least one peptide hormone selected from the group consisting of IGF-1, IGF-2 and GH and implanted into a mammal.

Alternatively, one may use gene therapy to transfect in vivo the recipient's cells. Formulations of nucleic acid for such in vivo methods may include: naked DNA; nucleic acid encapsulated into liposomes or liposomes combined with viral envelope receptor proteins (Nicolau et al., 1983, Proc. Natl. Acad. Sci. U.S.A. 80:1068); DNA coupled to a polylysine-glycoprotein carrier complex; and nucleic acid precipitants. Nucleic acid preparations may be introduced in vivo using any one of the techniques known in the art such as direct injection, electroporation, and particle bombardment. In addition, "gene guns" have been used for gene delivery into cells (Australian Patent No. 9068389).

A related approach might involve the use of modified gene therapy and viral vectors encoding the gene products for GLP-2 and at least one other peptide hormone selected from the group consisting of IGF-1, IGF-2 and GH. Such viral vectors may be used to infect remnant intestinal epithelium in patients with intestinal compromise, thereby effecting targeted local therapeutic delivery of these substances to the intestine in vivo. However, it is not necessary for the practice of the invention that all cells are transformed, or even that intestinal cells be transformed. Indeed, cells in any tissue which can secrete the chosen hormone into the circulatory system, for example muscle cells, may be used to endogenously produce hormones.

The sequence of such DNAs for the practice of gene therapy methods can readily be determined from the amino acid sequences of the selected GLP-2, IGF-1, IGF-2 and GH with the limitation that only forms containing genetically encoded amino acids can be produced in this manner. Various expression vectors, including viral vectors, suitable for introduction of genetic information into human cells, can be employed and will incorporate the DNA's encoding GLP-2, IGF-1, IGF-2 and GH under expression controls functional in the host cells. Once altered genetically, the engineered cells can then be implanted using procedures established in the art.

EXAMPLE 1

Effect of Rat GLP-2 on Small Intestine

This experiment was designed to investigate the effect of GLP-2 on small intestine growth. Mice were treated with human GLP-1, rat GLP-2, or no peptide, and the mass of the small intestine analyzed.

For this experiment, rat GLP-2 and human GLP-1 (7–36 amide) were custom synthesized by application of the tBoc-based solid phase approach. Analysis of the rat GLP-2 revealed a purity of 95% by analytical HPLC (20 mL) sufficient to dissolve the peptide completely. The pH was then readjusted to about 7.0 by addition of an equal volume of 1N NaOH (10–20 mL), and the solution volume was then adjusted to 10 mL by addition of distilled water. To prepare the formulation for injection, the 10 mL peptide solution and the 50 mL solution of 16% gelatin were combined with mixing, and aliquots for injection were drawn into a 0.5 mL insulin syringe. The same procedure was used to formulate the GLP-1, with the exception that no acid/base adjustment was necessary given its relative greater solubility in water.

Three groups of six mice (8 week old, CD1 females from Charles River Laboratories) were treated as follows. Each mouse received injections for 10 days. The injections were delivered subcutaneously in a final volume of 16% gelatin, with 0.5 cc injected subcutaneously every 12 hours. Mice treated with GLP-1 or GLP-2 peptide received 41.5 µg of the respective peptide in each injection. Control mice received 0.5 cc of 16% gelatin solution, but no peptide. Mice were fed standard rat chow with free access to food and water, until 12 hours prior to sacrifice, at which time food was withheld, and water only was given. The weight of the small intestine was ascertained by excising the entire intestine, and removing the stomach (proximal end) and appendix/cecum/large intestine (distal end). The remaining small intestine was cleaned with saline to remove feces, and weighed. Results are tabulated below:

TABLE II

| | Weight of Mice (gm) | | Small Intestine Weight | | |
| --- | --- | --- | --- | --- | --- |
| | Day 0 | Day 10 | Day 10 (gm) | Ave | % body wt |
| Control | 26.0 | 25.4 | 1.4 | 1.4 ± .04 | 5.47 ± .14 |
| | 27.0 | 25.9 | 1.3 | | |
| | 26.0 | 26.7 | 1.5 | | |
| | 25.6 | 24.4 | 1.4 | | |
| GLP-1 | 26.6 | 24.8 | 1.4 | 1.33 ± .04 | 5.26 ± .25 |
| | 23.2 | 22.8 | 1.3 | | |
| | 26.0 | 27.0 | 1.2 | | |
| | 25.1 | 26.5 | 1.4 | | |
| GLP-2 | 25.2 | 23.7 | 1.8 | 2.08 ± .14 | 8.12 ± .40 |
| | 27.1 | 25.7 | 2.3 | | |
| | 28.4 | 27.1 | 2.4 | | |
| | 25.8 | 25.4 | 1.8 | | |

These results demonstrate that, at a dose of about 2 mg/kg (about 500 nmole/kg), GLP-2 exhibits a statistically significant ($p\_0.05$) increase in the mass of small intestine after twice daily treatment for 10 days, relative both to the control group receiving no peptide, and to the group receiving another glucagon-related peptide, GLP-1. It is also clear that GLP-2 constitutes a major intestinal tissue growth factor.

EXAMPLE 2

Co-administration of GLP-2 with IGF-1 or GH

The following experiments were designed to investigate the effect on the intestinal mass of a mammal of co-administration of GLP-2 with IGF-1 or GH.

Forty-eight, six week old female CD1 mice (approx. 25 grams, obtained from Charles River Laboratories) were acclimatized in the animal facility for 1 week prior to the experiment. They were housed in plastic bottom, wire lid cages, maintained on a 12 hr light/dark cycle, and allowed chow and water, ad libitum throughout the study. Four days before starting the treatment the mice were weighed using a Mettler PJ300 scale and randomly allocated to 1 of 12 treatment groups. For the experiment, subcutaneous injections in the right hind quarter were given twice daily in the morning and evening for 10 days. However, Growth Hormone (GH) was administered only once a day in the morning. On day 10, the mice were fasted from 12 noon on. Body weight was also taken on day 5 and day 11.

The treatment groups consisted of the following peptides and peptide combinations. The amount of peptide received per dose by each animal is marked in beside each entry.
1. Control (PBS)
2. rGLP-2 (2.5 µg)
3. [Gly 2]hGLP-2 (2.5 µg)
4. IGF-1 (50 µg)
5. GH-(Protropin-Growth Hormone) (25 µg)
6. Insulin-like growth factor-1 analog (LRIGF-1) (50 µg)
7. IGF-1 (50 µg)+rGLP-2 (2.5 µg)
8. GH (25 µg)+rGLP-2 (2.5 µg)
9. LRIGF-1 (50 µg)+rGLP-2 (2.5 µg)
10. IGF-1 (50 µg)+[Gly 2] hGLP-2 (2.5 µg)
11. GH (25 µg)+[Gly 2] hGLP-2 (2.5 µg)
12. LRIGF-1 (50 µg)+[Gly 2] hGLP-2 (2.5 µg)

The peptides were weighed (Mettler AE166 scale), reconstituted and aliquoted on the day prior to the first injection. The injection volume, 0.5 ml, was constant through out the experiment using a ½ cc U-100 Insulin Syringe (Becton Dickinson and Company, N.J.). All peptide aliquots, except Protropin (GH), were kept at −20° C. and removed 60 minutes prior to injection to thaw. GH was kept at 4° C.

Control mice (group 1) received the same volume (0.5 ml) of phosphate buffered saline (PBS-1x-137 mM NaCl, 2.7 mM KCl, 4.3 mM Na2HPO4, pH 7.3). Peptides [rat GLP-2] (5 µg/ml) and human [Gly 2] GLP-2 (5 µg/ml) were reconstituted in PBS. One microliter of 1 N NaOH was required to dissolve [Gly2]hGLP-2 in 1 ml.

IGF recombinant peptides (IGF-1, Lot #FJF-103;Long R3IGF-1(LRIGF-1), Lot# HJF-A01 GroPep Pty Ltd., Australia) stock solutions were reconstituted in 10 mM HCl at a concentration of 1 mg/ml. To minimize the absorption of the peptide to the plastic surface, RIA Grade Bovine Serum Albumin (BSA) (BioLabs Lot 7943) was added to the PBS working solution (100 µg/ml BSA final concentration). Protropin (Growth hormone) (Lot C9009A2, Genentech Canada Inc., Burlington, ON) stock solution was reconstituted with Bacteriostatic water supplied in the kit. The working solution (50 µg/ml) was diluted in PBS (without BSA). Combination treatments of GH+rat GLP-2 and GH+ [Gly 2]hGLP-2 were administered by mixing 0.25 mls of each peptide, which were taken up into the same syringe to maintain a consistent injection volume of 0.5 ml. All other combination treatments (for example, rGLP-2+IGF etc.) were initially made up as separate solutions, mixed together, and frozen down together as aliquots of a single mixture, to be administered as single 0.5 ml injections.

Mice were sacrificed on day 11. Weight measurements were taken for the heart, kidneys, stomach, small intestine and large intestine. Small intestine length was also measured. Blood was taken via cardiac puncture and the plasma was frozen for future analysis. Tissues were also removed for histological analysis. Results were as followed:

TABLE III

Large Intestine Effect

| Treatment | Large Intestine Mass (g) | Change in Intestine Mass Relative to Control (g) | % Change Relative to PBS Control |
|---|---|---|---|
| PBS control | 0.283 | 0.000 | 0.000 |
| rat GLP-2 | 0.245 | −0.038 | −13.10 |
| [Gly 2] hGLP-2 | 0.308 | 0.025 | +9% |
| IGF-1 | 0.262 | 0.021 | −7% |
| hGH | 0.260 | 0.023 | −8% |
| LRIGF-1 | 0.285 | 0.002 | +1% |
| rat GLP-2 and IGF-1 | 0.318 | 0.035 | +12% |
| rat GLP-2 and hGH | 0.251 | −0.032 | −11% |
| rat GLP-2 and LRIGF-1 | 0.321 | 0.038 | +13% |
| [Gly 2] hGLP-2 and IGF-1 | 0.394 | 0.111 | +39% |
| [Gly 2] hGLP-2 and hGH | 0.352 | 0.069 | +24% |
| [Gly 2] hGLP-2 and LRIGF-1 | 0.400 | 0.117 | +41% |

These results clearly show that GLP-2 in combination with IGF-1 or GH acts synergistically to cause proliferation of large intestine.

TABLE IV

Small Intestine Effect

| Treatment | Small Intestine Mass (g) | Change in Intestine Mass Relative to Control (g) | % Change Relative to PBS Control |
|---|---|---|---|
| PBS control | 1.035 | 0.000 | |
| rat GLP-2 | 1.066 | 0.031 | +3 |
| [Gly 2] hGLP-2 | 1.810 | 0.775 | +75% |
| IGF-1 | 1.158 | 0.123 | +12% |
| hGH | 1.230 | 0.195 | +19% |
| LRIGF | 1.353 | 0.318 | +31% |
| IGF-1 | 1.517 | 0.482 | +47% |
| rat GLP-2/IGF-1 | 1.203 | 0.168 | +16% |
| rat GLP-2/hGH | 1.672 | 0.637 | +62% |
| [Gly 2] hGLP-2/IGF-1 | 1.901 | 0.866 | +84% |
| [Gly 2] hGLP-2/hGH | 1.705 | 0.670 | +65% |
| [Gly 2] hGLP-2/LRIGF | 2.258 | 1.223 | +118% |

From the above experiment it is also clear that [Gly 2]hGLP-2 in combination with IGF-1 or GH produces a proliferation of the small intestine which is greater than administration of the subject peptide alone. The results reported here for rat GLP-2 can be seen to be in error given the results presented in example 1 which have been successfully repeated.

EXAMPLE 3

Histological Analysis

Effects of co-administration of the peptide hormones of Example 1 was further explored histologically. The stomach, small intestine and large intestine of control and treated mice were examined using paraffin embedded sections and standard histopathological techniques. Three segments of small intestine consisted of proximal jejunum (8 cm distal to the pylorus), distal jejunum (18 cm distal to the pylorus), and distal ileum (10 cm before the cecum) and a segment of large intestine (proximal to the cecum) were taken. The tissues were fixed in 10% buffered formalin and embedded in paraffin using standard techniques. Four to six micron cross-sectional sections were cut and stained with hematoxylin and eosin. Intestinal micrometry was performed using the Leica Q500mc. Image Analysis System. Ten well-oriented villi from each section were used to determine villus height and crypt depths.

The results for the crypt+villus height in small intestine proximal jejunum are presented in FIG. 1. As can be seen, the increase in the height of the small bowel epithelial mucosa, expressed here as crypt plus villus height, observed following combination treatment with [Gly2]hGLP-2 and LRIGF-1 is greater than the crypt plus villus height obtained with either [Gly2]GLP-2 or LRIGF-1 alone.

EXAMPLE 4

Co-administration of GLP-2 with IGF-2

The effect of coadministration of IGF-2 with either rat GLP-2 or [Gly2)hGLP-2 is also investigated in mice. Groups of four mice are treated for 10 days as described in Example 2, except that the treatment groups and the initial dosages are as follows:
1. Control (PBS)
2. rGLP-2 (2.5 µg)

3. [Gly 2]hGLP-2 (2.5 μg)
4. LRIGF (50 μg)
5. IGF-2 (about 50 μg)
6. IGF-2 (about 50 μg)+rGLP-2 (2.5 μg)
7. IGF-2 (about 50 μg)+[Gly 2] hGLP-2 (2.5 μg)
8. IGF-2 (about 50 μg)+LRIGF (50 μg)
9. IGF-2 (about 50 μg)+(Gly 2] hGLP-2 (2.5 μg) +LRIGF (50 μg)

If necessary, the dose of IGF-2 may be decreased or increased approximately ten-fold to optimize the effect on intestine growth.

The results show that GLP-2 and GLP-2 analogs, when coadministered with IGF-2, show synergistic effects on the growth of the large intestine.

EXAMPLE 5

Endogenous Production of GLP-2

This experiment was designed to determine whether GLP-2 could be provided endogenously in intestinotrophic amounts by cells implanted into the mammal.

Cells from either the mouse enteroendocrine STC-1 cell line, or hamster islet InR1-G9 cells, or rat RIN1056A islet cells (Drucker et al. (1996) PNAS 93:7911–7916, and Ehrlich et al. (1994) Am. J. Physiol. 267:E662–E671), which secrete all of the glucagon-derived peptide hormones including GLP-2, were implanted subcutaneously on the back of a nude mouse. These cells grew as a solid tumor in vivo. Four weeks after implantation, the animals were sacrificed. The small intestine was removed, cleaned, and weighed. Comparison of the small intestine in the treatment group with control groups, either mice without tumors or mice with fibrosarcomas implanted subcutaneously that did not produce proglucagon-derived peptide hormones such as GLP-2, revealed that the small intestine mass increased significantly. Thus, this experiment showed that GLP-2 could be provided endogenously to a mammal by implanting GLP-2 producing cells. Additionally, GLP-2 produced subcutaneously by implanted cells exerted its intestinotrophic effects at a distal site in the small intestine. Other peptide hormones may be similarly provided to a mammal by implanting cells genetically engineered ex vivo to produce the peptide hormone, or inducing cells within the mammal to produce the peptide hormone through in vivo gene therapy.

EQUIVALENTS

The foregoing written specification is sufficient to enable one skilled in the art to practice the invention. Indeed, various modifications of the above-described means for carrying out the invention which are obvious to those skilled in the field of biology, medicine or related fields are intended to be within the scope of the following claims.

What is claimed is:

1. A composition for promoting the growth of small or large intestine tissue in a mammal, comprising GLP-2, or an intestinotrophic analog of GLP-2, in admixture with at least one other peptide hormone selected from the group consisting of IGF-1, analogs of IGF-1, IGF-2, analogs of IGF-2, GH, and analogs of GH, and a pharmaceutically acceptable carrier.

2. The composition according to claim 1, comprising GLP-2 and GH.

3. The composition according to claim 1, comprising GLP-2 and IGF-1.

4. The composition according to claim 3, comprising LRIGF-1.

5. The composition according to claim 1, comprising GLP-2 and IGF-2.

6. The composition according to claim 1, comprising an intestinotrophic GLP-2 analog.

7. The composition according to claim 1, wherein the GLP-2 and peptide hormone are present in an intestinotrophic amount.

* * * * *